Figure 1:
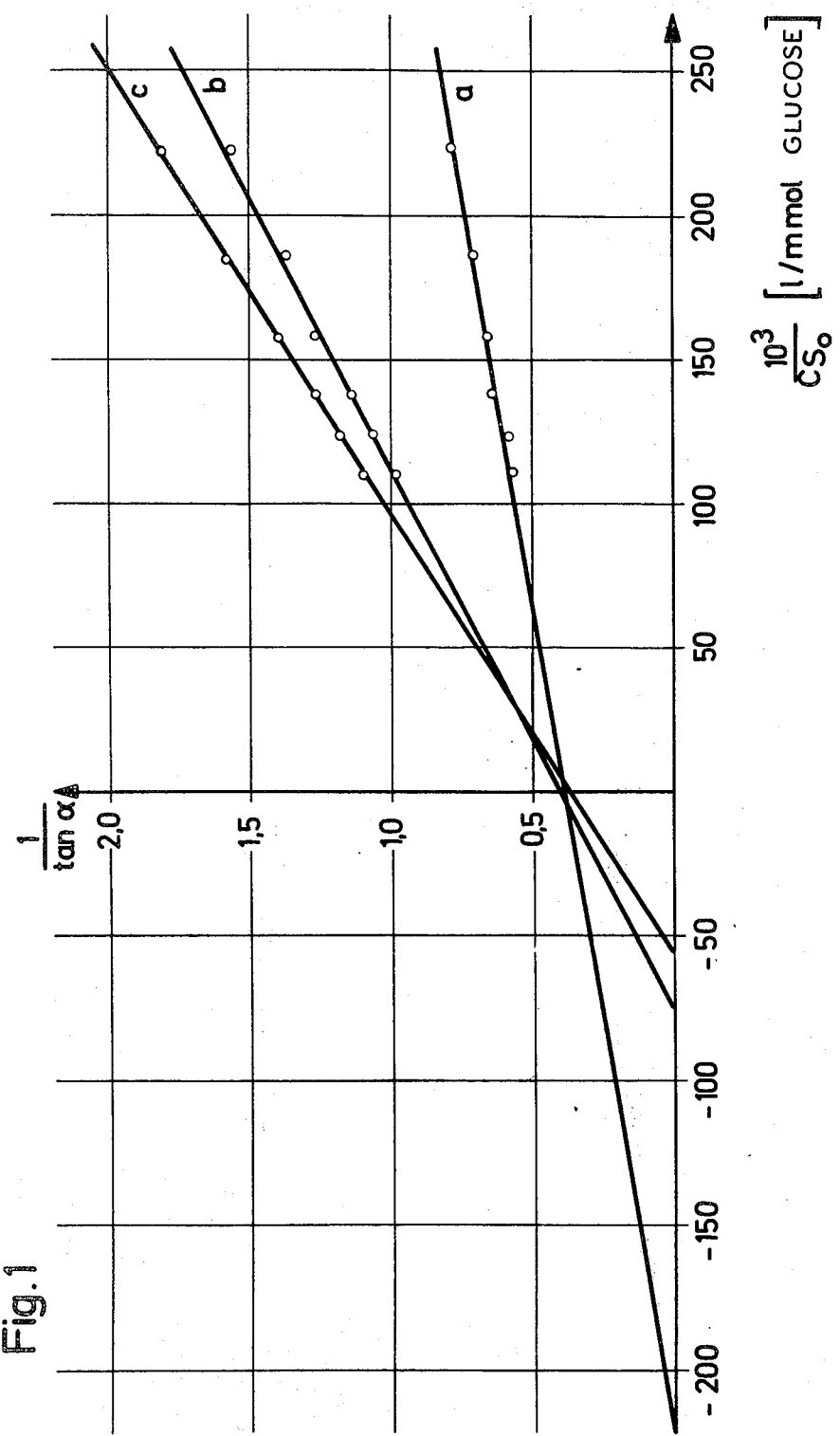

United States Patent [19]

Müller-Matthesius et al.

[11] 3,977,944

[45] Aug. 31, 1976

[54] ENZYME-KINETIC DETERMINATION OF THE CONCENTRATION OF A SUBSTRATE

[75] Inventors: Reinhard Müller-Matthesius, Hamburg-Norderstedt; Wolfgang Gruber, Unterzeismering, both of Germany

[73] Assignees: Eppendorf Geratebau Netheler & Hinz GmbH, Hamburg; Boehringer Mannheim G.m.b.H., Mannheim-Waldhof, both of Germany

[22] Filed: Oct. 2, 1974

[21] Appl. No.: 511,402

[30] Foreign Application Priority Data

Oct. 4, 1973 Germany............................ 2349819
Aug. 21, 1974 Germany............................ 2440011

[52] U.S. Cl............................ 195/103.5 R; 195/63; 195/99
[51] Int. Cl.²................ C12K 1/04; G01N 31/14; G01N 33/16
[58] Field of Search................. 195/103.5 R, 63, 99

[56] References Cited

UNITED STATES PATENTS 3,627,645  12/1971  Grassetti............... 195/103.5 R

OTHER PUBLICATIONS

Zollmer et al, "Heparin Determination With Ribonuclease", Methods of Enzymatic Analysis H. U. Bergmeyer, 1965, pp. 79–83.

Primary Examiner—David M. Naff
Assistant Examiner—C. A. Fan
Attorney, Agent, or Firm—Burgess, Dinklage & Sprung

[57] ABSTRACT

Enzyme-kinetic determination of the concentration of an enzyme substrate which is acted on during an enzymatic reaction is carried out by adding at least one competitive inhibitor to an enzymatic reaction medium to bring the ratio of the substrate concentration $C_3$ to the apparent Michaelis constant $K'_M$ to 0.2:1 or less, homogenizing the medium and determining the rate change of the enzymatic reaction at certain intervals of time.

25 Claims, 4 Drawing Figures

ENZYME-KINETIC DETERMINATION OF THE CONCENTRATION OF A SUBSTRATE

BACKGROUND

The invention relates to a method for the kinetic determination of the concentration of a dissolved or suspended substrate, wherein at least one enzyme is added and the speed of the enzymatic reaction is measured. The method is particularly suitable for the quantitative determination of substrates in blood serum or blood plasma. The invention furthermore concerns reagents for the practice of the method. The importance of the invention lies especially in the fields of clinical chemistry, biochemistry, food chemistry and pharmacy.

Especially in the analysis of biological liquids of complex composition, enzymatically catalyzed reactions are preferred for their substrate specificity in the reaction and for their high sensitivity.

On a routine basis, determinations of substrate concentration by means of enzymatically catalyzed reactions have hitherto usually been performed as end-value determinations, wherein a parameter is measured before and after the reaction to establish the difference between them.

The determination of uric acid by the Kageyama method, in which two enzymes are added, is an exception. What is kinetically measured, however, is the slow, nonenzymatic part of the action, so that this is basically different method. This known method takes a considerable amount of time, since measurements must be made after 6 and 12 minutes. This method is therefore expensive, inasmuch as an elevated temperature of 37°C has to be maintained. It would be advantageous if it were possible to perform this determination at the 25°C temperature usually used for the kinetic determination of enzyme activities, and thus to perform it with the apparatus already on hand.

Another exception is the determination of glucose with glucose oxidase, which can be performed kinetically with routinely used photometers, because the value of the Michaelis constant is exceptionally good for this reaction.

A kinetic determination of substrate concentrations, in which the change of a parameter is measured in the course of a reaction, offers important advantages over end-value determinations:

1. The amount of time required is shorter than in the corresponding end-value method.
2. A specimen blank value can usually be dispensed with, thereby reducing the number of steps required for the preparation of test solutions, reducing the consumption of specimen material and reagents, and in some cases reducing apparatus tie-up and on-line expense when computers are used.
3. Substrate determination can be performed with the apparatus commonly used for determining enzyme activity. This also makes possible the simultaneous performance of determinations which have hitherto been difficult to combine due to apparatus limitations.
4. The use of disposable cells, which eliminates rinsing and precludes contamination erros in the photometric measurements, is possible without restriction, because errors cannot occur due to differences in the inherent extinction of the cells.

In spite of all these obvious advantages, kinetic substrate determinations have not been routinely practiced and can be performed rationally only in exceptional cases. The known enzyme-kinetic techniques ("initial rate" and "time-fixed" techniques) are important only in research; they have it in common that only very small substrate concentration can be used and hence only very small substrate transformations can be measured.

The limitation to very small substrate concentrations in the test solution is necessary because only thus will there be a direct proportionality between the concentration of the substrate being tested and the speed of the reaction, i.e., only thus will a linear calibration curve be obtained, which is an essential requirement for simple routine determinations.

That is to say, the Michaelis-Menten equation $$v = \frac{v_{max} \cdot c_S}{c_S + K_M}$$

applies to the speed of enzymatically catalyzed reactions ($v$ = speed of reaction; $v_{max}$ = maximum speed in the substrate saturation range; $c_S$ = substrate concentration; $K_M$ = the Michaelis constant).

On the basis of this equation, proportionality will exist between the reaction speed $v$ and the substrate concentration $c_S$ only when $c_S$ is very small in relation to $K_M$. The term $c_S$ in the numerator can then be neglected, so that kinetically the result is a reaction of the pseudo-first order. As theoretical considerations show, $c_S$ may not be greater than 0.2 $K_M$ in order to keep the analytic error within acceptable limits for kinetic determinations.

Now, for most reactions, $K_M$ itself is very small, being of the order of magnitude of $10^{-3}$ to $10^{-7}$ moles per liter. It will be seen from this that measurements by the methods of the prior art are limited to extremely small substrate concentrations.

Attempts have been made to counter this difficulty by using enzymes having the highest possible value of $K_M$. The available selection, however, is small, and even in the most favorable case, the $K_M$ values are as a rule too low for substrate determinations in actual practice (the determination of glucose with GOD is one exception, as mentioned above).

From what has been stated above, the known kinetic enzyme methods suffer from the following disadvantages:

1. Extremely precise, expensive measuring instruments of high resolution are required, because the meter deflection in the case of very small substrate transformations is within the range of fluctuation of conventional apparatus such as photometers, for example.
2. Only the low portion of the concentration spectrum of the specimens can be tested without preliminary dilution; preliminary dilution is a source of additional errors and necessitates repetition of the analysis.
3. Dirt particles and air bubbles can greatly falsify the readings; in routine operations the necessary extreme cleanliness cannot always be assured.

THE INVENTION

The invention is addressed to the problem of devising a simple kinetic enzyme determination of substrate concentrations which will be suitable for routine tests, and of improving the former methods by making them generally applicable and enabling them to perform measurements within practical lengths of time, as well as to cover a greater range of concentrations without additional preliminary dilution.

This problem is solved in accordance with the invention by a method for the kinetic enzyme determination of the concentration of a substrate, especially a substrate dissolved or suspended in blood serum or blood plasma, in which one or more substrate-specific enzymes are added and the speed of the enzymatic reaction is measured, the said method being characterized in that, by the addition of at least one competitive inhibitor specific for the speed-determining step of the enzymatic substrate reaction, the ratio of the substrate concentration $c_S$ to the apparent Michaelis constant $K_M'$ is made equal to or less than 0.2:1, thereby approximating the conditions of a reaction of the pseudo-first order, the mixture is homogenized, the change in a reaction parameter specific for the reaction is determined at specified intervals of time, and the substrate concentration is derived therefrom.

Preferably, the ratio of $c_S$ to $K_M'$ is brought to a value below 0.05 : 1, especially below 0.01 : 1.

The term "competitive inhibitors", as used herein, refers to two groups of substances:
a. Substances which (in accordance with the law of mass action) compete reversibly with the substrate for the enzyme, but are transformed not at all or with negligible slowness (competitive inhibitors in the conventional sense).
b. Substances which reversibly bind the substrate and thereby diminish its free concentration (in accordance with the law of mass action), the inhibitor-substrate complex not being transformed by the effect of the enzyme.

As suitable competitive inhibitors, substances are preferably selected which are structurally related to one of the starting substances and/or one of the end products of the speed-determining reaction, but are not made to react by the enzyme used in this reaction.

In the method of the invention, the measurement is made more precise by a greater transformation of the substrate. It can be performed by simple means. The measurement time can advantageously range from 0.5 to 3 minutes. The proportionality between reaction speed and substrate concentration is approached closely enough to achieve an accuracy sufficient for analytic purposes.

The versatility and adaptability of the method is considerably improved over known methods by the fact that by controlling the ratio of concentrations of substrate to enzyme to competitive inhibitor the measurement can be made sufficiently sensitive for analytical purposes, even at a low substrate concentration, and the measurement can be performed within a reasonable length of time.

In this connection, an advantageous embodiment provides, on the one hand, for an improvement of the proportionality between the speed of the reaction and higher substrate concentrations by the addition of the inhibitor, and on the other hand compensates for the loss of reaction speed by increasing the enzyme concentration. An increase in the reaction speed might also be achieved by increasing the reaction temperature.

Despite the use of a competitive inhibitor, the increase in the enzyme concentration will have a desirable effect if the sensitivity is to be increased and a greater transformation is to be tested, which in turn leads to an improvement of the proportionality between reaction speed and substrate concentration in the specimen. In particular, the increase in the enzyme concentration does not have to be acquired at the cost of a disproportionately short measuring time, since the speed of the reaction can be controlled in a flexible manner through selection of the concentration of the competitive inhibitor. In accordance with the invention this brings the decisive advantage of being able to test at higher substrate concentrations within a practical measuring time with conventional apparatus. Especially, it is possible by an appropriate selection of the amount of specimen, the concentration of the enzyme and the concentration of the inhibitor, to measure the entire relevant concentration range of a substrate in the specimen without dilution before or after.

Practitioners of the art have hitherto completely overlooked the possibility of utilizing this effect of competitive inhibitors in kinetic enzyme determinations. In retrospect, the effect can be explained by introducing into the numerator of the above-described Michaelis-Menten equation another additive term:

$$v = \frac{V_{max} \cdot c_S}{c_S + K_M + K_M \cdot c_I / K_I}$$

wherein $$K_I = \frac{c_{SI}}{c_S \cdot c_I}$$

if the substrate is bound, and $$K_I = \frac{c_{EI}}{c_E \cdot c_I}$$

if the enzyme is bound. Also:
$c_I$ = concentration of the inhibitor,
$c_{SI}$ = concentration of the substrate-inhibitor complex,
$c_S$ = concentration of the free substrate.
$c_{EI}$ = concentration of the enzyme-inhibitor complex,
$c_E$ = free enzyme concentration.

Since the term $K_M + K_M \cdot c_I \cdot K_I$ (apparent Michaelis constant $K_M'$) is always greater than $K_M$, the proportionality between reaction speed $v$ and substrate concentration $c_S$ in a defined period can be achieved at higher substrate concentrations than is possible without the addition of a competitive inhibitor.

In accordance with the invention, the concentration of the free enzyme and the ratio $c_{EI} : c_E$ or $c_{SI} : c_S$ are so adjusted to the substrate concentration that measurements can be made with sufficient sensitivity within a reasonable time at an adequate proportionality. An important advantage of the invention consists in the fact that the sensitivity can be controlled not only by means of the substrate and enzyme concentrations but also by means of the concentration of the competitive inhibitor.

From this point of view a sensitivity sufficient for the reliable detection of small substrate concentrations is advantageously established by means of the ratio of the substrate concentration $c_s$ to the enzyme concentration $c_E$ to the competitive inhibitor concentration $c_I$.

If the end of any extended creep or drift is not to be awaited, it is desirable to correct for creep by recording a blank value.

The measurement is best performed, preferably by the "time fixed" technique, immediately after homogenization of the mixture and compensation of any rise in temperature that may occur. In this technique, the measurements are performed over an equal period of time after a certain chosen lapse of time, in all of the measurements in one series of analyses, within the range of the pseudo-first order reaction. Preferably, after the chosen period of time, an averaging is performed of the readings obtained during the measuring period, or a kinetic two-point measurement is performed at the beginning and end of the period, or a determination is made of the momentary rate of transformation at an established moment of time, e.g., by determining the angle of rise of the curve of measurement. The time may be any period within the first-order type of reaction, but it must be made equal for all measurements of a series of analyses. Therefore, practical, short measuring periods can be selected. In particular, it is possible to establish an appropriate, and even short, measuring periods as required. It is also possible to determine the initial rate of transformation (the "initial rate" technique).

Under certain circumstances it may be desirable to add not just one inhibitor but a plurality of inhibitors.

It is also possible to apply the method of the invention to multi-stage reactions, in which not all of the stages have to be enzymatically catalyzed. For example, the substrate that is to be detected can be made to react in an enzymatic step for rate determination, which will be followed by a rapid nonenzymatic indicator reaction. In this case the inhibitor is added to the first (enzymatic) reaction. A similar procedure is followed when the indicator reaction also is enzymatically catalyzed. Now, however, there is a second possibility, which is to allow the first stage to run its course quantitatively and thus store up its reaction products; then the second stage is examined kinetically with the addition of an inhibitor designed for the second stage.

In an especially advantageous embodiment, a buffer is used which is adapted to the mixture to be used for the measurement. On account of the partial reaction that is possible in various cases, the pH of the buffer is selected to match, insofar as possible, the pH rate maximum with respect to the overall rate of reaction of the mixture being measured and to avoid any marked reduction of the $K_M$ value of the enzyme.

An especially surprising effect of the method of the invention furthermore is that any inhibitors that may already be present in the specimen, which might falsify the results of the analysis, can be greatly offset by increasing the inhibitor concentration. Such falsifying effects are important in actual practice, because, for example, many of the drugs present in patients' blood serum can have an inhibitive effect. Accompanying substances which occur naturally often have an inhibiting action, too. The method of the invention thus offers a way of obtaining correct analysis results even in those cases in which an unknown inhibitor is present in an unknown amount.

Additional subject matter of the invention is therefore a method of the kind initially described, which is characterized by the use of a solution of the substrate to be tested, which already exercises a competitive inhibiting effect on the enzyme used for the determination. Preferably, in this case, the intentioanlly added competitive inhibitor is used in an amount which produces a 60 to 95% inhibition of the enzyme. The best results in this case are obtained when the substrate solution being tested already exercises an inhibiting effect on the enzyme used for the determination, amount to as much as a 50% inhibition of the said enzyme.

The method of the invention for the kinetic enzyme determination of substrates in the presence of unknown inhibitors by the addition of known inhibitors in a known amount is highly surprising, and overcomes the prejudice of practitioners of the art who have believed that the kinetic determination of substrates in the presence of unknown inhibitors is impossible. For example, it is known from Analytical Chemistry, 31, p. 980 (1959), that the presence of activities inhibiting the enzyme-catalyzed reaction is the most important problem in the enzymatic determination of substrates, and that such determination cannot be performed when unknown and unspecific inhibiting agents are present. It is particularly stated that inhibiting agents themselves can no longer be determined when they contain other inhibiting impurities.

For the practice of this embodiment of the method, the information given above is applicable in the same manner. It is desirable, however, to perform a preliminary test of an unknown specimen to determine whether it already contains inhibiting activities capable of inhibiting the enzyme by not more than 50%. This can be done simply by adding a known amount of substrate and a known enzyme activity. If at least 50% of the added substrate is then determined kinetically or by end-value determination, the method of the invention can be used without having to allow for a markedly greater error than if the measurement were performed in an inhibitor-free solution. If appreciably less than 50% is determined, the method of the invention can still be practiced, but a somewhat greater error must be allowed for. In the latter case it is desirable to raise the amount of intentionally added inhibitor to the upper limit of the applicable inhibition range, which is approximately 95%. If the foreign inhibitions are less than 40%, such an amount of competitive inhibitor will preferably be added that an enzyme inhibition between 65 and 85% is achieved.

Also subject matter of the invention is a reagent for the kinetic enzyme determination of the concentration of a substrate by the method of the invention. Such a reagent contains a system for the enzymatic measurement of this substrate, and it is characterized by a content of at least one competitive inhibitor of the enzyme-substrate reaction being measured. The known systems for the enzymatic determination of substrates by the end-value method, which are commercially available in many forms, are basically suitable for this reagent. The reagent of the invention contains, in addition to such a system, at least one competitive inhibitor. The inhibitor and the enzyme can be present in the form of a common complex which brings about an additional stabilization of the enzyme similar to the substrate stabilization of an enzyme.

A system for the enzymatic measurement of a substrate generally contains an enzyme specific for the substrate, a buffer adapted to this enzyme, and in some cases cofactors and/or auxiliary enzymes and/or stabilizers. The term "cofactor," as used herein, refers to coenzymes, including metal ions acting as coenzymes, and cosubstrates.

The reagents or combinations of reagents in accordance with the invention may be either in the form of solutions or in the form of lyophilized, freeze-dried mixtures. An especially desirable embodiment is achieved by packaging lyophilized reagents in disposable cells which, upon the addition of a solvent (e.g., the buffer), are immediately ready for use, and are discarded after the determination has been performed.

EXAMPLES

The following examples describing in detail a uric acid determination and a glucose determination are given for further explanation of the invention. In an analogous manner, triglyceride, for example, can be determined by the glycerokinase method, urea can be determined by the urease-G1DH method, cholesterol can be determined by the cholesterol dehydrogenase method, or lactate can be determined by the LDH method. Other enzymatic determinations which can be performed kinetically in accordance with the invention will be found, for example, in H.U. Bergmeyer, "Methoden der enzymatischen Analyse," Verlag Chemie Weinheim, 1974.

EXAMPLE 1

Photometric Determination of Uric Acid by the Uncoupled Uricase Reaction

The reaction involved is the following:

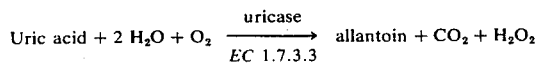

The magnitude to be measured is the uric acid extinction near its absorption maximum at 293 nm.

Apparatus

Eppendorf enzyme measurement appartus 5086 (photometer with filter Hg 302 nm, multiplier 1 P 28 and spectral lamp Hg 15). Eppendorf pipettes and specimen-reagent proportioner.

Reagents

1. Potassium thiocyanate
2. Uric acid
3. Lithium carbonate
4. 0.1 mole/l borate buffer, pH 9.5
5. Uricase 5 U/ml (prepared from swine liver)

Procedure

Determination of type of inhibitor 50 microliters of standard solution containing 0.178, 0.297, 0.476, 0.595, 0.733, 0.892 and 1.19 millimoles of uric acid per liter (prepared by diluting with double distilled water a stock solution of 5.95 mmoles/l uric acid in 54 moles/l lithium carbonate) are incubated in the cell at 25°C with 500 µl of buffer without inhibitor in the one case, and 500 µl of 103 mmoles/l potassium thiocyanate in buffer in the other, and the reaction was started by the admixture of 50 µl of uricase diluted 1:10 in double distilled water. Recording is started 20 seconds after initiation of the reaction: paper speed 2 cm/min, spread 20 cm for E=0–1. With an angle measuring means, the angle $\alpha$ formed with the time axis is measured at the beginning of each recording. The reciprocals of tan $\alpha$ are plotted as ordinates against the corresponding reciprocal uric acid concentrations (Lineweaver-Burk diagram). The calibration straight line is drawn through the points obtained with and without the addition of potassium thiocyanate. If a competitive type of inhibitor is present the prolongation of the straight lines must intersect the ordinates at the same point.

Optimation of Test Conditions

50 µl of the standard solutions are incubated with 500 µl of 825 mmoles/l potassium thiocyanate in buffer at 25°C, the reaction is started by the addition of 50 µl of undiluted uricase, and the measurement is performed as above. For the determination of the apparent Michaelis constant, the reciprocals of the tangent $\alpha$ are plotted as ordinates, and the reciprocal molar substrate concentrations in the test mixture as abscissae. The apparent Michaelis constant is found as a negative reciprocal of the abscissae intersections of the straight lines of regression (insertion of suitable small values for $1/c_S$ followed by graphic evaluation). The value of the apparent Michaelis constant $K_M'$ is important in judging the maximum uric acid concentration usable in the test, which is to be as far below 0.05 $K_M'$ as possible.

Results and Discussion

On the basis of 17 µmoles/l uric acid for the Michaelis constant of uricase obtained from swine liver (T.O. Tiffany et al., Anal. Chem. 45, 1716-23 (1973)), the maximum usable concentration will be 0.85 µmole/l uric acid if the $c_S$:$K_M$ ratio is taken to be 0.05 for the determination of the initial rate. If one sets out from a test volume of 600 µl, the amount of serum used must be limited to 0.85 µl in order to be able to measure up to a content of 0.6 mmoles/l of uric acid in the serum without additional predilution. Aside from the fact that the serum has to be prediluted because such a small volume of 0.85 µl cannot be directly measured out with accuracy, under these conditions, even in the end-value method, at the lowermost normal value limit for human serum (0.12 mmoles/l uric acid) an extinction of only 0.002 can be achieved, with respect to the extinction coefficient of uric acid 12.6 cm²/µmole at 293 nm (Boehringer Mannheim GmbH., Test Manual, 3rd Ed., 1969, Section on Uric Acid). The process is too insensitive for a kinetic determination.

It is true that the use of bacterial uricase allows the initial concentration to be increased by a factor of 6. Sufficient sensitivity, however, will result only if the first measuring point is recorded 4 seconds after the start of the reaction and a "time-fixed" interval of 1.5 minutes or more is selected (Tiffany, loco citato).

In potassium thiocyanate a suitable competitive inhibitor (same ordinate intersection in the Lineweaver-Burk plotting method for the same enzyme activity) has been found which, in a concentration of 687 mmoles per liter of test solution, has produced an apparent Michaelis constant of 1 mmole/l. In the case of a 50 µl undiluted specimen and a test volume of 600 µl, a $c_S/K_M$ value of 0.05 is calculated for the concentration 0.6 mmoles/l uric acid in the specimen, so that, with regard to sensitivity and linearity of the calibration curve, the requirements for a simple routine method appear to be satisfied.

In harmony with this calculation, for the reading of the angle at 20 seconds, proportionality has been found between the tangent and concentrations up to 0.6 mmoles/l uric acid in water with an error of −3% for the highest content, which can be tolerated if it is desired to apply the conditions to the analysis of serum. The angle amounted to about 8° at the normal value limit under the conditions, so that the sensitivity of the process is also sufficient for small substrate concentrations.

The conditions established for aqueous solutions of uric acid can thus be the same for serum analysis. Prior to the addition of the uricase, the creep due to oxidation of the ascorbic acid contained in variable amounts in the serum must be awaited.

By increasing the inhibitor concentration the linear measurement range can be extended and the accuracy at higher uric acid concentrations can be increased, and at the same time the sensitivity should be improved by changing to the 293 nm mwasuring wavelength and/or by further increasing the enzyme activity and/or increasing the temperature.

EXAMPLE 2

Photometric Determination of Glucose by the Glucose-Dehydrogenase Method

The following known reaction is involved:

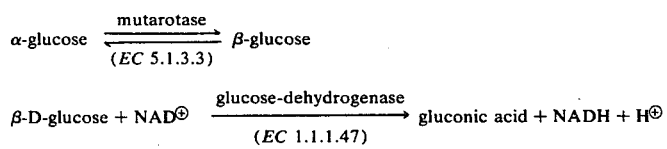

Apparatus

Eppendorf Enzyme Measuring Apparatus 5086 (kinetic determinations), Eppendorf Substrate Measuring Apparatus 5091 (end value determinations), Eppendorf pipettes or Eppendorf specimen-reagent proportioner (microliter range), calibrated transfer pipettes (milliliter range). Laboratory pH meter made by Knick. Combitron S table top computer made by Diehl with program for average, standard deviation and variation coefficient as well as a special program (Archiv No. 10344) for linear regression, correlation coefficient and scatter about the straight line of regression.

Reagents

1. Potassium thiocyanate
2. Potassium chloride
3. Disodium salt of ethylenedinitrilotetraacetic acid
4. D(+)-glucose, anhydrous, high purity
5. Aqueous glucose standard solution
6. Nicotinamide-adenine-dinucleotide, free acid (150 mg/ml $H_2O$)
7. "Blood Sugar, GlucDH Method" (Merckotest packaged test).

Solutions

1. Buffer: 120 mmoles/l phosphate buffer, pH 7.6
2. Buffer-Enzyme Mixture: Solution of glucose-dehydrogenase and mutarotase in buffer, prepared as described in pamphlet accompanying the test package.
3. Stablized buffer-enzyme-inhibitor mixture: Solution containing 825 mmoles potassium thiocyanate and 55 mmoles of the disodium salt of ethylenedinitrilotetraacetic acid per liter of buffer-enzyme mixture. pH: 6.6.

Procedure

1. Characterization of the glucose-dehydrogenase activity

20 μl of buffer-enzyme mixture diluted 1 : 10 with buffer was incubated with 500 μl of 280 mmoles of glucose per liter of buffer (substrate inhibition at higher glucose concentrations) and the rate of increase of the extinction was followed for three minutes after the admixture of 20 μl of 150 mmoles/l $NAD^+$.

Computation and results ($\epsilon$ = molar extinction NADH, $d$ = layer thickness, EV = test volume, PV = specimen volume, F = dilution factor):

$$U/ml = \frac{\Delta E}{min} \cdot \frac{10^3}{\epsilon \cdot d} \cdot \frac{EV}{PV} \cdot F = 0.205 \cdot \frac{10^3}{3.3 \cdot 10^3 \cdot 1.00} \cdot \frac{540}{20} \cdot 11 = 18.5$$

2. Type of inhibitor

100 μl standards containing 27.8, 33.3, 38.8, 44.4, 50.0 and 55.5 mmoles glucose per liter were incubated in the cell with 500 μl of the following solutions: (a) Buffer-enzyme mixture, diluted 1 : 40 with buffer, (b) 410 mmoles/l potassium thiocyante in dilute buffer-enzyme mixture, (c) 620 mmoles/l potassium thiocyanate in dilute buffer-enzyme mixture (the solutions containing thiocyanate were prepared freshly each time). The reaction was started by the admixture of 20 μl of 200 mmoles/l $NAD^+$, and recording was begun 10 seconds later: paper feed 5 cm/min, spread 20 cm for E = 0 − 1.

For the determination of the angle $\alpha$ with the axis of time the virtually linear initial area of the recording was evaluated; for the determination of the type of inhibitor, the reciprocals of tangent $\alpha$ (identical with the initial rate, for practical purposes) were plotted as ordinates and the reciprocals of the millimolar glucose concentrations used in the test were plotted as abscissae (Lineweaver-Burk diagram).

To clear up the question as to whether the thiocyanate ion is responsible for the inhibiting action, potassium thiocyanate was replaced by the equimolar amount of potassium chloride.

3. Determinations of Concentration

General Test Mixture:

20 μl of specimen was incubated in the cell at 25°C with 500 μl of stabilized buffer-enzyme-inhibitor mixture and the reaction was started by the admixture of 20 μl $NAD^+$ (150 mg/ml $H_2O$). 20 seconds after the start of the reaction, recording was performed at a paper feed of 5 cm/min at Hg 366 nm, and the layer thickness 1.00 cm, and the angle $\alpha$ was determined 20 seconds after the start of the reaction in each case.

Computation on the standard containing 5.55 mmoles of glucose per liter:

$$S_{0; \text{ specimen}} = \tan \alpha \text{ specimen} \frac{5.55}{\tan \alpha \text{ standard}}$$

Analysis of Human Plasma:

The specimens used were human plasmas which had been obtained by the centrifugation of venous blood stabilized with fluoride-EDTA-benzoic acid.

Parallel analyses were performed by the hexokinase end value method with dealbumination in accordance with Eppendorf Instruction AV 707 — T; in a departure from the instruction, the calculations were performed on the standard.

DISCUSSION OF THE RESULTS

Potassium thiocyanate as competitive inhibitor

FIG. 1 shows a Lineweaver-Burk diagram (ordinates: reciprocal rise of the extinction-time curve 10 seconds after start of reaction, abscissae: reciprocal millimolar glucose concentration in the test). The prolongation of the lines found without the addition of inhibitor (a), with the addition of 330 mmoles KSCN per liter of test solution (b), and with the addition of 500 mmoles KSCN per liter of test solution (c) intersect the ordinates at virtually the same point, while the abscissae intersection approaches the origin as the inhibitor concentration increases, which is the characteristic of the competitive type of inhibitor.

Range of Measurement and Sensitivity

Figure 2A:
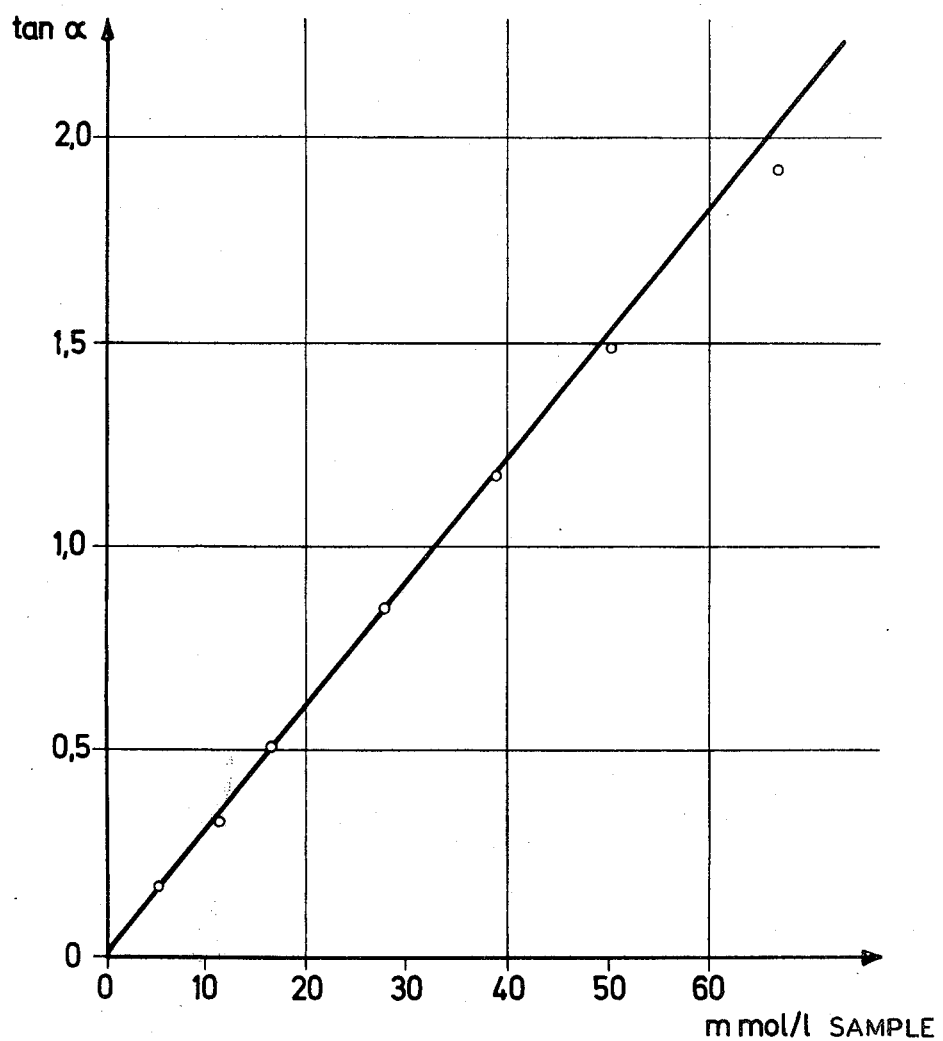
Figure 2B:
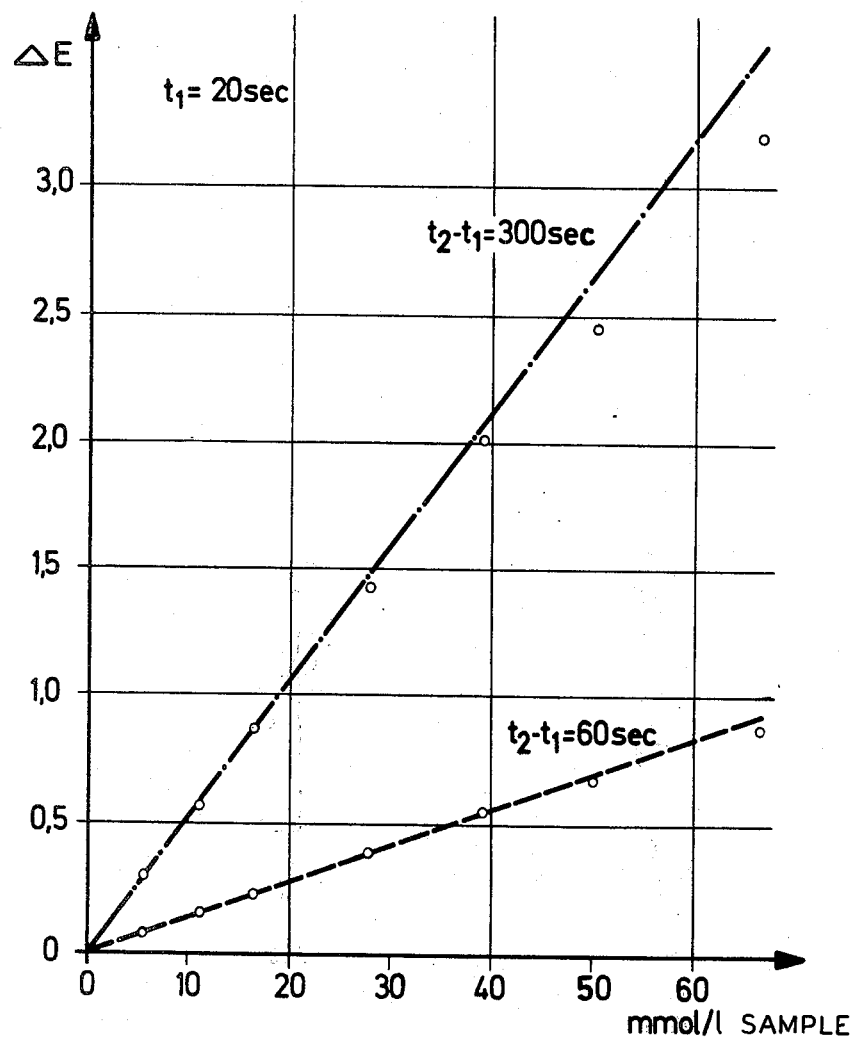

In FIGS. 2a and 2b are represented calibration curves which result when the apparent Miachaelis constant is adjusted to 50 mmoles of glucose per liter by the addition of inhibitor: in the one case for the rise of the extinction-time curve 20 seconds after the start of the reaction, and in the other case for the fixed-time interval of 60 and 300 seconds, respectively, each, again, 20 seconds after start of the reaction (paper feed 10 cm/min; measuring wavelength Hg 366 nm).

For the practical practice of the method the following points are important:

1. If one accepts an error of 3% far above the normal value limit (approx. 5 mmoles per liter of specimen), the dilution limit for the angle reading or the shorter "time fixed" interval will be at 50 mmoles per liter, and thus much more favorable than in the various end value methods of the prior art.

In the case of the 300-second interval, the linearity of the calibration curve is sufficient up to about 20 mmoles per liter. If the conditions remain the same, however, one can go only slightly beyond this limit, because:

2. The extinction difference becomes too great for the range of routinely used photometers, especially when the inherent extinctions of the specimens must be heeded in mechanized measurements. By changing the test conditions (e.g., higher inhibitor concentration, smaller amount of specimen), however, the sensitivity can be reduced and at the same time the concentration coverage can be extended.

In the case of the angle reading, the sensitivity must, and in the case of the 60-second interval the sensitivity should, be increased by measuring closer to the NADH absorption maximum and/or by reducing the paper feed speed. The sensitivity reserves of the method are so great that the usable concentration range, even in the case of brief measurement duration, is limited only by the measuring range of the photometer or by the reading limit of routinely used angle measuring instruments, it being unnecessary to increase the enzyme concentration beyond that specified by the manufacturer of the reagent.

Correctness and Precision

The correctness of the method was verified with the aid of the refinding rate, by comparative measurements by the hexokinase end value method, and by means of control serums.

The refinding rate (Table 1) must be considered to be very good. For the parallel measurement by the hexokinase end value method, plasma was used, because the glucose-dehydrogenase reaction is inhibited, for a reason which is not yet clear, if blood cells get into the test mixture to any great extent (although preliminary tests have shown that the kinetic determination can be performed under modified conditions after dealbumination, so that whole-blood analysis is also possible). The direct use of plasma (or serum, as the case may be) aids in the rapid performance of the measurement as well as simultaneous kinetic determinations in general with other substrates or enzymes.

Table 1

Refinding rates when glucose is weighed into Qualtrol. Concentrations given in millimoles of glucose per liter of specimen.

| Concentration weighed in | Found | After deducting the natural content | Refinding rate |
|---|---|---|---|
| 31.4 | 37.7 | 31.8 | 101.5% |
| 15.7 | 22.0 | 15.9 | 101.0% |
| 12.5 | 18.5 | 12.6 | 100.5% |
| 8.99 | 15.1 | 9.21 | 102.0% |
| 5.24 | 11.2 | 5.27 | 100.5% |

Figure 3:
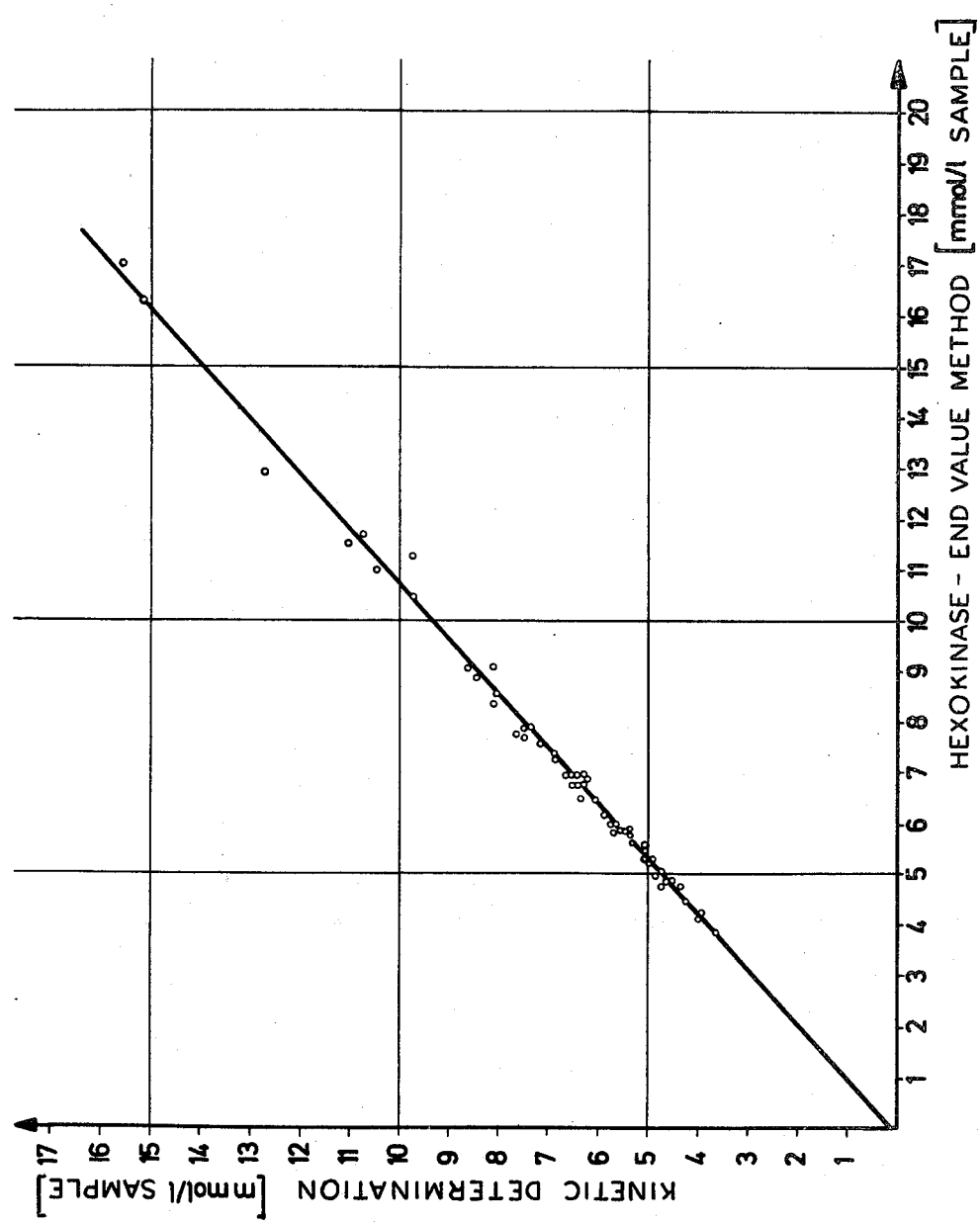

From the results of the comparative tests performed on 60 human plasmas (concentration ranging from about 4 to 16 millimoles per liter of plasma, cf. FIG. 3, showing the correlation between glucose determination by a direct kinetic method and by the indirect hexokinase end value method), the regression line was computed as $y = 0.1255 + 0.9272 x$, the correlation coefficient significantly different from zero as $r = +0.9965$, and the scatter around the regression line as $S_{x,y} = 0.2085$. According to these figures there is a close correlation between the two methods. The results for the kinetic determination, however, average 7% lower, virtually independently of concentration, than the concentration values, computed on the same standard, of the end value method. This difference is in harmony with the volume displacement effect in the case of dealbumination.

It is interesting to make a comparison with the corresponding values of whole blood analysis from routine, which have been obtained by the hexokinase end value method with dealbumination, in which the factor used for the computation was 2.5% below the factor "theoretically" applicable to aqueous glucose solutions. In comparison with the kinetic analysis, an average minus was found of 14%, and even of 20% in comparison with plasma analysis by the hexokinase end value method.

The glucose concentrations found on five control serums by the kinetic method were always slightly higher than the declared standard values (Table 2), except for Precinorm S. The result obtained with Hyland Control Serum can perhaps be explained by low standard values, such as are typical for the glucose-oxidase method.

Table 2

Analysis of control serums. Concentrations and standard deviations are given in millimoles of glucose per liter.

| Serum | declared $\bar{x}$ | declared $\bar{x} \pm 2s$ | n | found $\bar{x}$ | found s | VK |
|---|---|---|---|---|---|---|
| Hyland Control Serum II | 11,4[1] | 10,5–12,2 | 12 | 12,44 | 0,25 | 2,0 |
| Monitrol II | 11,6[2] | 10,7–12,5 | 12 | 11,89 | 0,32 | 2,7 |
| Precinorm S | 5,95 | 5,35–6,55 | 12 | 5,86 | 0,13 | 2,2 |
| Pathotrol | 13,9[2] | 13,2–14,6 | 12 | 14,67 | 0,29 | 2,0 |
| Labtrol | 5,15[2] | 4,80–5,50 | 12 | 5,37 | 0,16 | 3,0 |

[1]Glucose-oxidase (Hyland)
[2]HK/G6P-DH end value method with dealbumination (Boehringer)

Table 2 also gives the precision in the series which was found on control serums and which, according to our experience, is comparable with the hexokinase end value method which was also performed manually.

The day-to-day precision was determined on Precinorm S at VK = 3.4%.

EXAMPLE 3

The exclusion of the interference of foreign inhibitors that can be achieved by the invention is illustrated by the measurements obtained for two different enzymes and two different inhibitors each, which are listed in the following two tables.

Table 3

| Kinetic glucose determination with GlucDH | | |
|---|---|---|
| KSCN millimoles | Phloretin micromoles | Average inhibition in % |
| 310 | — | 78 |
| — | 1.4 | 20 |
| 310 | 1.4 | 81 |
| 38.5 | — | 17 |
| — | 14 | 76 |
| 38.5 | 14 | 78 |

Table 4

| Kinetic uric acid determination with uricase | | |
|---|---|---|
| KSCN millimoles | Xanthine micromoles | Average inhibition in % |
| 500 | — | 82 |
| — | 20 | 34 |
| 500 | 20 | 82 |
| 10 | — | 17 |
| — | 80 | 76 |
| 10 | 80 | 72 |
| 40 | — | 41 |
| — | 40 | 60 |
| 40 | 40 | 62 |

Tables 3 and 4 show that the inhibitor that is present in each case in an amount that produces an inhibition of at least 60% completely suppresses the influence of the second inhibitor which is present in an amount producing less than 50% inhibition, and only the inhibiting action of the dominant inhibitor comes into play.

EXAMPLE 4

Kinetic glucose determination with glucose-dehydrogenase

The following test mixture was used:
0.12 mole phosphate buffer pH = 7.6
40 millimoles sulfosalicylic acid
55 millimoles EDTA
150 millimoles NAD
0.86 millimole – 2.59 millimoles glucose
1.8 U glucose-dehydrogenase
0.31 mole KSCN or
1.4 nanomoles phloretin
Table 5 shows the results of the measurements.

Table 5

| Glucose mmoles [S] | No inhibitor ΔE/min | No inhibitor % inh. | 0.31 mole KSCN ΔE/min | 0.31 mole KSCN % inh. | 1.4 nmoles phloretin ΔE/min | 1.4 nmoles phloretin % inh. |
|---|---|---|---|---|---|---|
| 2.59 | 75.4 | — | 17 | 77.5 | 62.5 | 17.1 |
| 1.72 | 54.0 | — | 10.5 | 80.6 | 45.5 | 15.8 |
| 1.29 | 40.6 | — | 8.0 | 80.3 | 30.0 | 26.0 |
| 0.86 | 31.1 | — | 4.5 | 85.5 | 24.0 | 22.8 |

| | 0.31 mole KSCN + 1.4 nmoles phloretin ΔE/min | % inhibition |
|---|---|---|
| 2.59 | 16.0 | 78.8 |
| 1.72 | 10.5 | 80.6 |
| 1.29 | 7.0 | 82.7 |
| 0.86 | 5.0 | 83.9 |

EXAMPLE 5

Kinetic glucose determination with glucose-dehydrogenase

The following test mixture was used:
90 mmoles phosphate buffer pH = 7.6
40 mmoles sulfosalicylic acid
55 mmoles EDTA
4.65 mmoles NAD
0.86 – 3.45 mmoles glucose
95 mU glucose dehydrogenase
38.5 mmoles KSCN
14 nmoles phloretin
Table 6 shows the results of the testing.

Table 6

| Glucose mmoles [S] | No inhibitor ΔE/min | % inh. | 38.5 mmoles KSCN ΔE/min | % inh. | 14 nmoles phloretin ΔE/min | % inh. |
|---|---|---|---|---|---|---|
| 3.45 | 108.3 | — | 90 | 17 | 26.7 | 75 |
| 2.59 | 78.7 | — | 72.3 | 8 | 20.3 | 76 |
| 1.72 | 63.3 | — | 49.7 | 21.69 | 14.0 | 78 |
| 1.29 | 49.7 | — | 40.3 | 18.8 | 11.3 | 77 |
| 0.86 | 33.7 | — | 28.0 | 17 | 8.7 | 74 |

| | 14 nmoles phloretin plus 38.5 mmoles KSCN | |
|---|---|---|
| | ΔE/min | % inhibition |
| 3.45 | 27.7 | 75.5 |
| 2.59 | 19.7 | 75 |
| 1.72 | 15.7 | 75 |
| 1.29 | 10.7 | 78.5 |
| 0.86 | 5.7 | 83 |

EXAMPLE 6

Inhibition of Uricase
The following test mixture was used:
96 mmoles borate buffer pH = 9.5
114 – 7.6 μmoles uric acid
29 mU uricase/ml
0.5 mole KSCN
0.02 mmoles xanthine
The results of the tests are shown in Table 7.

Table 7

| Uricase [S] | No inhibitor ΔE/min | % inh. | 0.5 mole KSCN ΔE/min | % inh. | 0.02 mmole xanthine ΔE/min | % inh. |
|---|---|---|---|---|---|---|
| 114 μmole | 171 | — | 46 | 73 | 127 | 26 |
| 38 μmole | 87 | — | 16.3 | 81 | 66 | 25 |
| 7.6 μmole | 23 | — | 3.3 | 86 | 14 | 49 |

| | 0.5 mole KSCN plus 0.02 mmole xanthine | |
|---|---|---|
| | ΔE/min | % inhibition |
| 114 μmole | 44.5 | 74 |
| 38 μmole | 15.0 | 83 |
| 76 μmole | 3.0 | 87 |

What is claimed is:

1. Method for the enzyme-kinetic determination of the concentration of a substrate wherein one or more specific enzymes are added and the rate of the enzymatic reaction is measured, the improvement which comprises adding at least one competitive inhibitor inhibiting the rate determining step of the enzymatic substrate reaction to bring the ratio of the substrate concentration $c_S$ to the apparent Michaelis constant $K_M'$ of the inhibited enzymatic reaction to 0.2 : 1 or less, thereby establishing the conditions of a pseudo-first order reaction, homogenizing the mixture, determining the change in a reaction parameter specific for the reaction at certain intervals of time, and calculating the concentration of the substrate to be detected therefrom.

2. Method of claim 1 wherein the ratio of the substrate concentration $c_S$ to the apparent Michaelis constant $K_M'$ is brought to a value of 0.05 : 1 or less.

3. Method of claim 1 wherein a competitive inhibitor is used which reversibly binds the enzyme without being chemically reacted.

4. Method of claim 3 wherein a competitive inhibitor is used which is chemically similar to one of the starting products of the measuring reaction.

5. Method of claim 1 wherein a competitive inhibitor is chosen to result in a ratio of the concentration of substrate to enzyme permitting a sensitivity suitable for analytical measurement.

6. Method of claim 1 wherein the sensitivity of the measurement is increased by increasing the enzyme concentration.

7. Method of claim 1 wherein the determination is performed immediately after homogenizing the mixture, waiting for the end of any abrupt temperature rise.

8. Method of claim 1 wherein any extended creep that may occur is corrected by recording a blank value.

9. Method of claim 1 wherein a buffer adapted to the measuring mixture is used, the pH value of said buffer coinciding substantially with the pH-rate-maximum of the total reaction rate of the measuring mixture.

10. Method of claim 1 wherein within the range of the pseudo-first order reaction, in all measurements in a series of analyses, the measurement is performed in an equal period of time after a certain chosen time after the start of the reaction ("time fixed" technique).

11. Method of claim 1 wherein within one series of analyses, one performs, after the certain chosen time, an averaging of the measures values determined in the measuring period, or a kinetic two-point measurement at the beginning and end of the time period, or a determination of the momentary rate at a set point in time.

12. Method of claim 1 wherein the initial rate is determined ("initial rate" technique).

13. Method of claim 1 wherein the competitive inhibitor or inhibitors and the enzyme are dissolved in a buffer adapted to the measuring mixture, this solution is added to the serum, and thereafter a co-substrate is added.

14. Method of claim 1 wherein a solution of the substrate to be determined is used, which already displays a competitive inhibiting effect.

15. Method of claim 14 wherein the competitive inhibitor is added in an amount which produces a 60 to 95% inhibition of the enzyme.

16. Method of claim 14 wherein a substrate solution is used which inhibits the enzyme up to 50%.

17. Method of claim 1 wherein said substrate is dissolved or suspended in blood serum or plasma.

18. Method of claim 1 wherein the ratio of the substrate concentration $c_S$ to the apparent Michaelis constant $K_M'$ is brought to a value of 0.01 : 1 or less.

19. Method of claim 1 wherein a competitive inhibitor is used which reversibly binds the substrate without being chemically reacted.

20. Method of claim 3 wherein a competitive inhibitor is used which is chemically similar to one of the end products of the reaction.

21. Method of claim 1 wherein the sensitivity of the measurement is increased by increasing the reaction temperature.

22. Method of claim 1 wherein the determination is performed immediately after homogenizing the mixture and waiting for the cessation of any creep that may occur.

23. Reagent for an enzyme-kinetic determination of the concentration of an enzyme substrate consisting essentially of uricase, buffer, potassium thiocyanate and lithium carbonate.

24. Reagent for an enzyme-kinetic determination of the concentration of an enzyme substrate consisting essentially of
    phosphate buffer;
    sulfosalicyclic acid;
    EDTA;
    NAD;
    glucose;
    glucose-dehydrogenase;
    potassium thiocyanate; and
    phloretin.

25. Reagent for an enzyme-kinetic determination of the concentration of an enzyme substrate consisting essentially of
    borate buffer;
    uric acid;
    uricase;
    potassium thiocyanate; and
    xanthine.

* * * * *